US010456111B2

(12) United States Patent
Lee et al.

(10) Patent No.: US 10,456,111 B2
(45) Date of Patent: *Oct. 29, 2019

(54) ULTRASOUND SYSTEM AND SIGNAL PROCESSING UNIT CONFIGURED FOR TIME GAIN AND LATERAL GAIN COMPENSATION

(75) Inventors: Doo Sik Lee, Seoul (KR); Mi Jeoung Ahn, Seoul (KR)

(73) Assignee: Samsung Medison Co., Ltd., Hongchun-gun, Kangwon-do (KR)

( * ) Notice: Subject to any disclaimer, the term of this patent is extended or adjusted under 35 U.S.C. 154(b) by 1049 days.

This patent is subject to a terminal disclaimer.

(21) Appl. No.: 13/586,290

(22) Filed: Aug. 15, 2012

(65) Prior Publication Data

US 2013/0064036 A1    Mar. 14, 2013

Related U.S. Application Data

(63) Continuation-in-part of application No. 13/184,094, filed on Jul. 15, 2011, now Pat. No. 8,403,855, which
(Continued)

(30) Foreign Application Priority Data

Dec. 7, 2006 (KR) .................. 10-2006-0123752

(51) Int. Cl.
*A61B 8/00* (2006.01)
*G06F 3/01* (2006.01)
(Continued)

(52) U.S. Cl.
CPC ............... *A61B 8/467* (2013.01); *A61B 8/00* (2013.01); *A61B 8/46* (2013.01); *A61B 8/461* (2013.01);
(Continued)

(58) Field of Classification Search
CPC ........... A61B 8/00; A61B 8/14; A61B 8/4254; A61B 8/4444; A61B 8/461; A61B 8/463;
(Continued)

(56) References Cited

U.S. PATENT DOCUMENTS 4,043,181 A    8/1977  Nigam
4,475,400 A   10/1984  Flax
(Continued)

FOREIGN PATENT DOCUMENTS

EP    0 539 697 A1    5/1993
EP    1 219 972 A2    7/2002
(Continued)

OTHER PUBLICATIONS

United States Office Action issued in U.S. Appl. No. 13/938,847 dated Oct. 8, 2013.
(Continued)

*Primary Examiner* — Amanda Lauritzen Moher
(74) *Attorney, Agent, or Firm* — Morgan, Lewis & Bockius LLP

(57) ABSTRACT

A hydraulic unit of an electronic control brake system including a modulator block; a pair of master cylinder connection portions; a first valve row having a plurality of first valve accommodation bores; a second valve row having a plurality of second valve accommodation bores; a pair of low-pressure accumulator bores arranged in a bottom side of the modulator block in the lateral direction; pump accommodation bores; a pair of shuttle valve ESV accommodation bores arranged between the first valve row and the second valve row; a pair of driving force control valve TC accommodation bores arranged between wheel cylinder connection portions formed in the modulator block and the first valve row; and a pair of high-pressure accumulator bores arranged in the modulator block in a longitudinal direction,
(Continued)

wherein the pair of high-pressure accumulator bores are formed to have an arrangement parallel to the motor accommodation bores.

36 Claims, 9 Drawing Sheets

Related U.S. Application Data is a continuation of application No. 11/857,860, filed on Sep. 19, 2007, now Pat. No. 8,016,759.

(51) Int. Cl.
| | |
|---|---|
| *G06F 3/0484* | (2013.01) |
| *G06F 3/048* | (2013.01) |
| *G06T 7/00* | (2017.01) |
| *G06T 7/50* | (2017.01) |
| *G01S 7/52* | (2006.01) |
| *G06F 3/0488* | (2013.01) |
| *G06F 3/0489* | (2013.01) |
| *A61B 6/00* | (2006.01) |
| *G06T 7/90* | (2017.01) |

(52) U.S. Cl.
CPC .............. *A61B 8/463* (2013.01); *A61B 8/465* (2013.01); *A61B 8/469* (2013.01); *G01S 7/52033* (2013.01); *G01S 7/52073* (2013.01); *G01S 7/52074* (2013.01); *G01S 7/52084* (2013.01); *G06F 3/01* (2013.01); *G06F 3/048* (2013.01); *G06F 3/0484* (2013.01); *G06F 3/0488* (2013.01); *G06F 3/04845* (2013.01); *G06F 3/04847* (2013.01); *G06F 3/04883* (2013.01); *G06F 3/04886* (2013.01); *G06F 3/04897* (2013.01); *G06T 7/0012* (2013.01); *G06T 7/50* (2017.01); *A61B 6/467* (2013.01); *G06T 7/90* (2017.01); *G06T 2200/24* (2013.01); *G06T 2207/10132* (2013.01)

(58) Field of Classification Search
CPC ..... A61B 8/467; A61B 8/5207; A61B 8/5269; A61B 8/54; A61B 8/465; A61B 8/46; A61B 6/467; A61B 8/4405; A61B 8/464; A61B 8/466; A61B 8/469; G01S 7/52033; G01S 7/52084; G01S 7/52073; G01S 7/52074; G06T 7/0012; G06T 2200/24; G06T 2207/10132; G06T 2207/20104; G06T 2207/20208; G06T 3/40; G06T 3/60; G06T 5/009; G06T 7/50; G06T 7/90; G06F 3/048; G06F 3/04845; G06F 3/01; G06F 3/0484; G06F 3/04847; G06F 3/04883

See application file for complete search history.

(56) References Cited

U.S. PATENT DOCUMENTS

| | | | |
|---|---|---|---|
| 4,817,614 A | | 4/1989 | Hassler et al. |
| 5,161,535 A | | 11/1992 | Short et al. |
| 5,245,586 A | | 9/1993 | Hassler |
| 5,315,999 A | | 5/1994 | Kinicki et al. |
| 5,482,045 A | | 1/1996 | Rust et al. |
| 6,063,030 A | * | 5/2000 | Vara .............. A61B 8/468 600/437 |
| 6,102,859 A | | 8/2000 | Mo |
| 6,142,942 A | | 11/2000 | Clark |
| 6,368,279 B1 | * | 4/2002 | Liu .............. A61B 8/00 600/443 |
| 6,468,212 B1 | * | 10/2002 | Scott et al. .............. 600/437 |
| 6,677,985 B1 | | 1/2004 | Kubota et al. |
| 6,933,934 B2 | * | 8/2005 | Amemiya .............. A61B 8/4411 345/179 |
| 7,022,075 B2 | | 4/2006 | Grunwald et al. |
| 8,016,759 B2 | | 9/2011 | Lee et al. |
| 8,403,855 B2 | | 3/2013 | Lee et al. |
| 2002/0008692 A1 | | 1/2002 | Omura et al. |
| 2002/0087218 A1 | * | 7/2002 | Amemiya .............. A61B 8/4411 700/19 |
| 2003/0097071 A1 | | 5/2003 | Halmann et al. |
| 2003/0187353 A1 | * | 10/2003 | Ng et al. .............. 600/437 |
| 2003/0236459 A1 | | 12/2003 | Loftman et al. |
| 2004/0015079 A1 | | 1/2004 | Berger et al. |
| 2005/0059892 A1 | | 3/2005 | Dubois et al. |
| 2007/0230759 A1 | | 10/2007 | Tamura |
| 2007/0239019 A1 | | 10/2007 | Richard et al. |
| 2009/0043195 A1 | | 2/2009 | Poland |
| 2009/0069677 A1 | | 3/2009 | Chen et al. |
| 2010/0145195 A1 | | 6/2010 | Hyun |
| 2011/0054325 A1 | | 3/2011 | Shin et al. |
| 2013/0030298 A1 | | 1/2013 | Tamura |
| 2013/0064036 A1 | | 3/2013 | Lee et al. |
| 2013/0144169 A1 | | 6/2013 | Lee et al. |
| 2014/0088428 A1 | * | 3/2014 | Yang et al. .......... A61B 8/4444 600/443 |
| 2014/0164965 A1 | * | 6/2014 | Lee ............... G06F 3/04842 715/765 |
| 2016/0139789 A1 | * | 5/2016 | Jin ............... G06F 3/04847 715/771 |

FOREIGN PATENT DOCUMENTS

| | | |
|---|---|---|
| JP | 6-154227 A | 6/1994 |
| JP | 10-248843 A | 9/1998 |
| JP | 2000-197637 A | 7/2000 |
| JP | 2006-296978 A | 11/2006 |
| KR | 2001-0067091 A | 7/2001 |
| KR | 2004-0069378 A | 8/2004 |
| KR | 2006-0033845 A | 4/2006 |

OTHER PUBLICATIONS

United States Office Action issued in U.S. Appl. No. 13/938,847 dated Mar. 21, 2014.
U.S. Office Action issued in related U.S. Appl. No. 13/475,686 dated Mar. 26, 2015.
U.S. Office Action issued in U.S. Appl. No. 138475,686 dated Aug. 2, 2013.
U.S. Final Office Action issued in U.S. Appl. No. 13/475,686 dated Mar. 13, 2014.
Non-Final Office Action U.S. Appl. No. 14/866,038 dated Jan. 5, 2016.
U.S. Office Action issued in U.S. Appl. No. 13/938,847 dated Jun. 10, 2015.
U.S. Office Action dated Aug. 12, 2016 issued in U.S. Appl. No. 13/756,274.
U.S. Office Action issued in U.S. Appl. No. 13/756,274 dated Aug. 12, 2016.
U.S. Office Action dated Jul. 1, 2016 issued in U.S. Appl. No. 14/866,038.
U.S. Office Action dated Feb. 26, 2016 issued in U.S. Appl. No. 13/756,274.
Non-Final Office Action dated Feb. 26, 2016 for U.S. Appl. No. 13/756,274, filed Jan. 31, 2013.
U.S. Non-Final Office Action dated Aug. 7, 2017 issued in U.S. Appl. No. 13/756,274.

\* cited by examiner

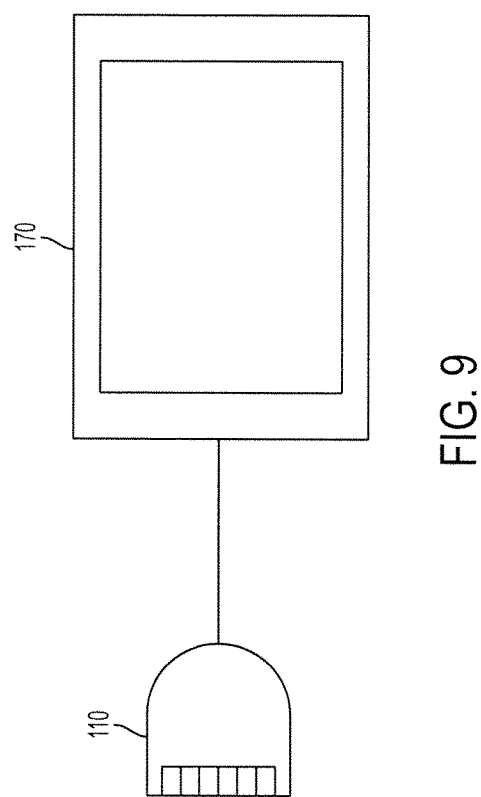

ULTRASOUND SYSTEM AND SIGNAL PROCESSING UNIT CONFIGURED FOR TIME GAIN AND LATERAL GAIN COMPENSATION

The present application is a Continuation-In-Part application of U.S. application Ser. No. 13/184,094 filed on Jul. 15, 2011, which is a continuation application of U.S. application Ser. No. 11/857,860 filed on Sep. 19, 2007, now U.S. Pat. No. 8,016,759, which claims priority from Korean Patent Application No. 10-2006-0123752 filed on Dec. 7, 2006, the entire subject matter of which is incorporated herein by reference.

BACKGROUND

1. Field

The present disclosure generally relates to an ultrasound system, and more particularly to an ultrasound system adapted to precisely and easily perform TGC (Time Gain Compensation) and LGC (Lateral Gain Compensation).

2. Background

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional diagnostic images of internal features of an object.

In order to transmit and receive ultrasound signals, the ultrasound system is generally provided with a probe including a wideband transducer. When the transducer is electrically stimulated, it produces ultrasound signals and transmits them into a human body. The ultrasound signals transmitted into the human body are reflected from borders between human tissues and then returned to the transducer. The returned ultrasound echo signals are converted into electric signals. Thereafter, ultrasound image data for imaging the tissues is produced by amplifying and signal-processing the echo signals.

Typically, the ultrasound system is provided with a control panel including a plurality of input units in order to perform a control function of acquiring the ultrasound image, a menu control function, a measurement and annotation function, etc. The control panel is comprised of a touch panel, an image control unit, a measurement control unit, etc. The touch panel displays menus for optimizing an ultrasound image displayed on a display unit. The menus on the touch panel can be touched and selected by a user. The image control unit controls the ultrasound image, whereas the measurement control unit measures a distance to the object, a circumference of the object, etc. As illustrated in FIG. 1, the image control unit includes a plurality of TGC control keys 11 and a plurality of LGC control keys 12. The TGC control keys 11 are used to control a gain of each echo signal based on depth of the position from which the echo signal is reflected. Further, since the echo signal attenuated at the outer right and left sides, the LGC control keys 12 are used to control a gain of the attenuated echo signal.

In the conventional system, the TGC control keys 11 and the LGC control keys 12 are arranged on different areas of the control panel. The problem associated with such an arrangement is that the size of the control panel must be inevitably increased. Further, a user of the system suffers a great inconvenience when operating the TGC control keys 11 and the LGC control keys 12. Another problem of the conventional system is that since the TGC control keys 11 and the LGC control keys 12 are comprised of slide-type variable resistors, it is very difficult for an unskilled user to finely control TGC and LGC with the TGC control keys 11 and the LGC control keys 12.

In order to resolve the above problems, the present invention is directed to providing an ultrasound system adapted to display a setup screen used to input TGC and LGC curves on a touch panel and perform TGC and LGC based on the inputted TGC and LGC curves.

The present invention provides an ultrasound system, which comprises: a signal acquiring unit adapted to transmit an ultrasound signal to an object and acquire an echo signal reflected from the object; a signal processing unit adapted to perform TGC (Time Gain Compensation) and LGC (Lateral Gain Compensation) upon the echo signal at a coarse compensation mode based on predetermined TGC and LGC values; an image producing unit adapted to produce an ultrasound image of the object based on the TGC and LGC compensated echo signal; an input unit adapted to allow a user to provide TGC and LGC curves; and a TGC/LGC setup processor adapted to set TGC and LGC values based on the TGC and LGC curves provided by the user. The signal processing unit is further adapted to perform the TGC and LGC upon the echo signal at a fine compensation mode based on the TGC and LGC values set by the TGC/LGC setup processor.

In addition, the present disclosure provides an ultrasound system, which comprises: a processor adapted to configure a setup screen for display; and a touch panel adapted to display the setup screen so as to allow a user to input TGC and LGC curves. The processor is further adapted to calculate the TGC and LGC values based on the inputted TGC and the LGC curves.

BRIEF DESCRIPTION OF THE DRAWINGS

Arrangements and embodiments may be described in detail with reference to the following drawings in which like reference numerals refer to like elements and wherein:

FIG. 9 illustrates a block diagram of an ultrasound system employing a portable computer.

DETAILED DESCRIPTION

A detailed description may be provided with reference to the accompanying drawings. One of ordinary skill in the art may realize that the following description is illustrative only and is not in any way limiting. Other embodiments of the present disclosure may readily suggest themselves to such skilled persons having the benefit of this disclosure.

Certain embodiments of the present disclosure will be explained below with reference to FIGS. 2 to 8.

Figure 1:
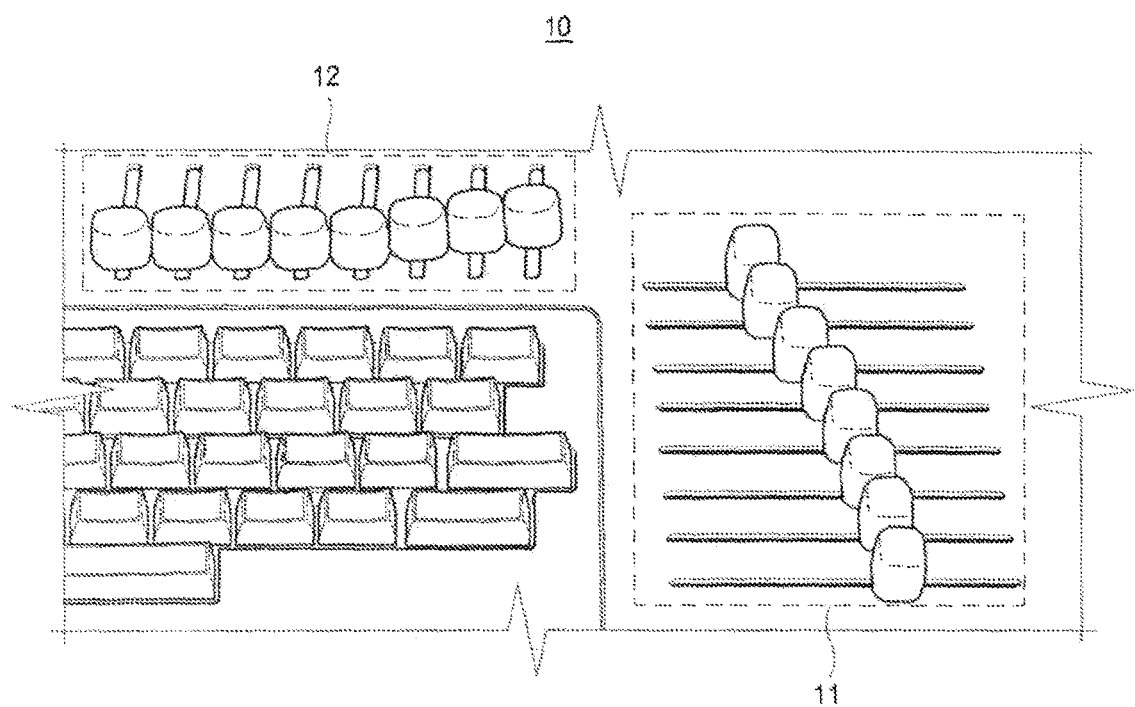
FIG. 1 is a schematic diagram illustrating conventional TGC and LGC control keys.
Figure 2:
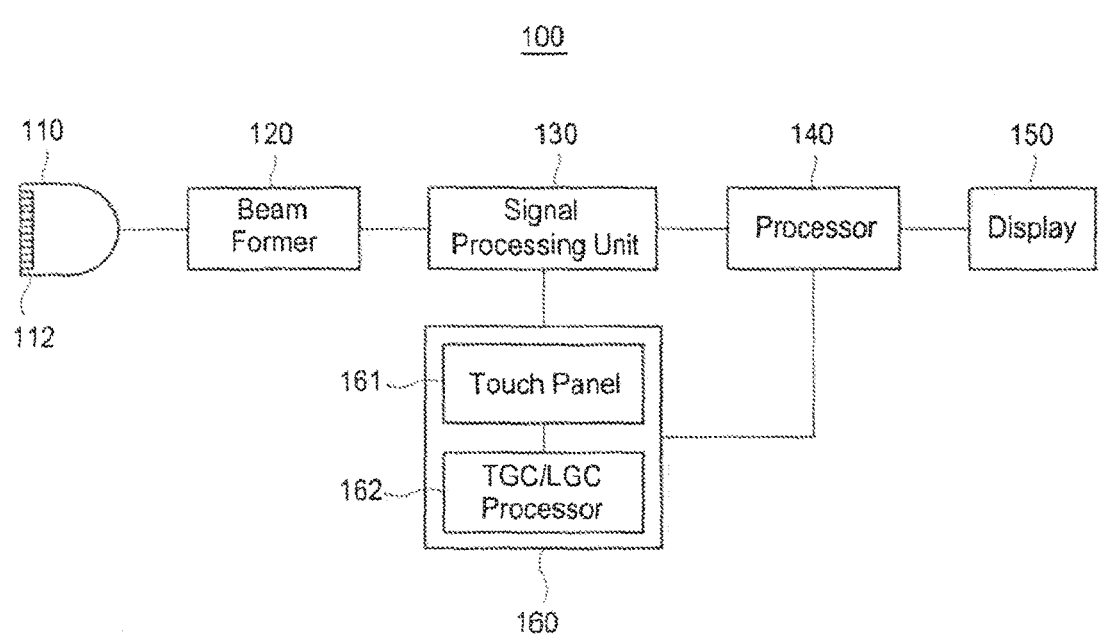
FIG. 2 is a block diagram showing a structure of an ultrasound system according to one embodiment of the present disclosure.
Figure 3:
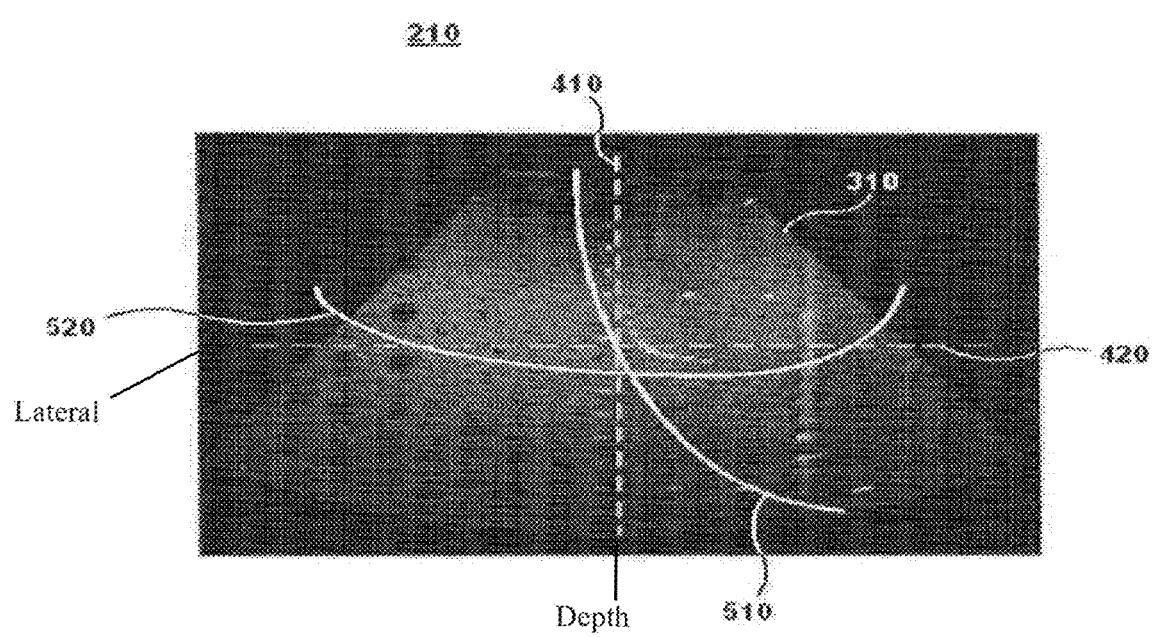
FIGS. 3 to 7 illustrate a setup screen according to one embodiment of the present disclosure.
Figure 4:
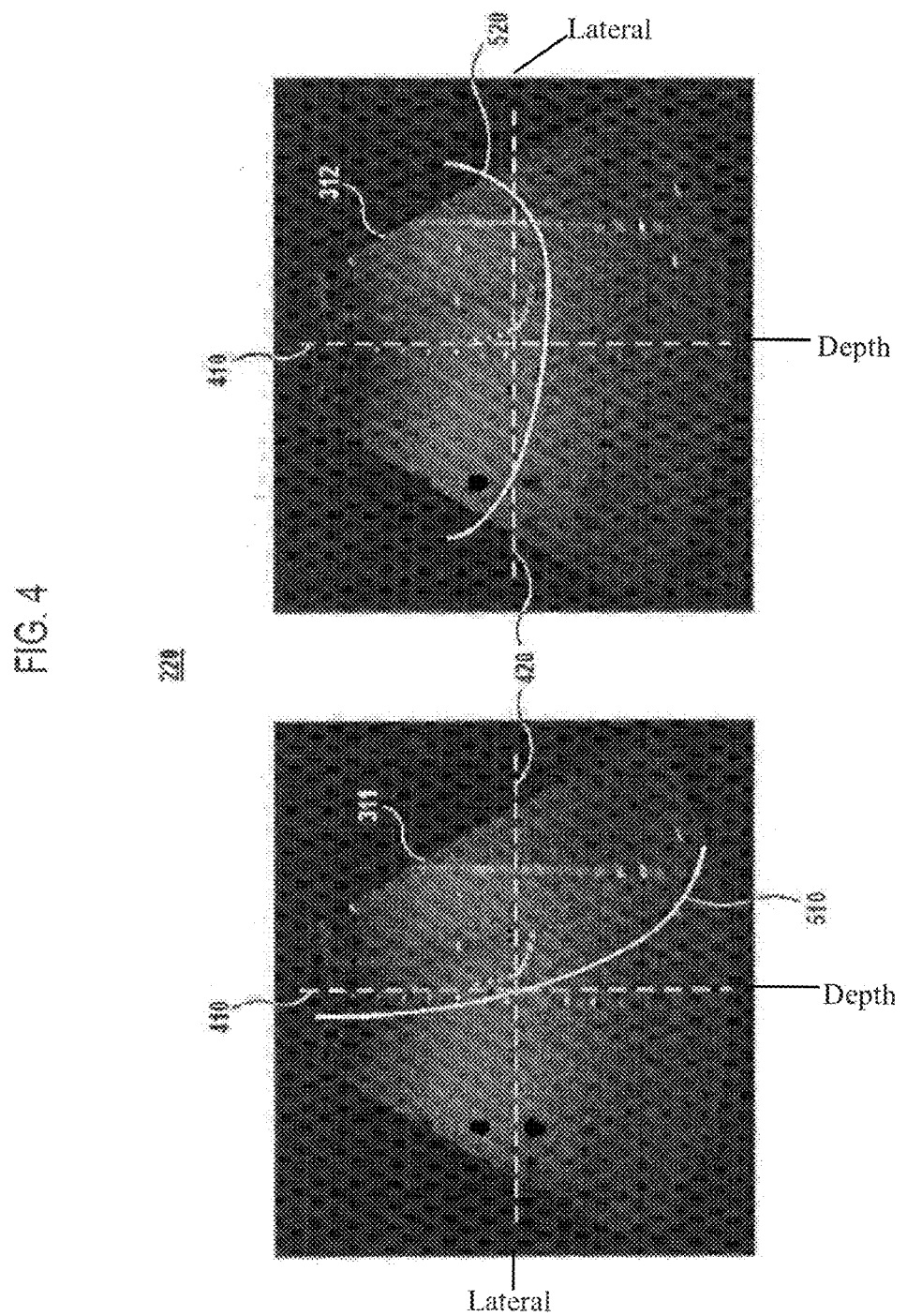
Figure 5:
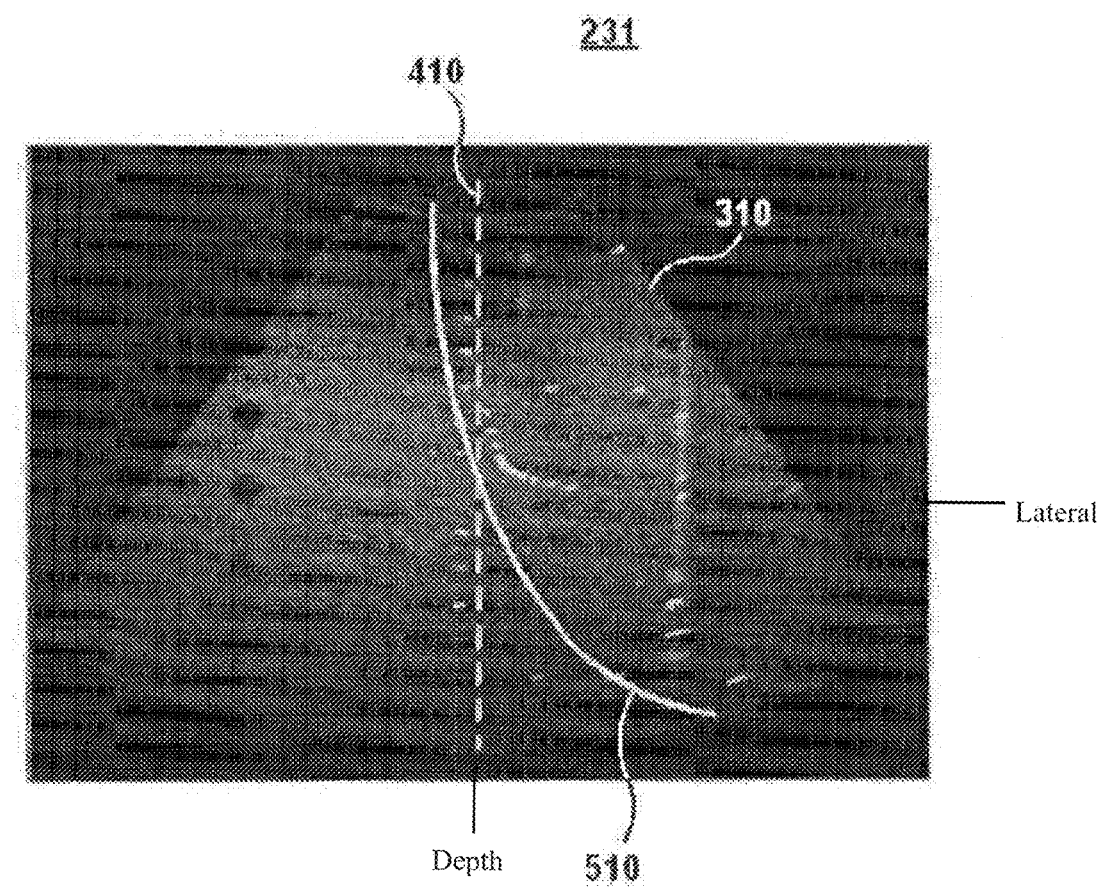
Figure 6:
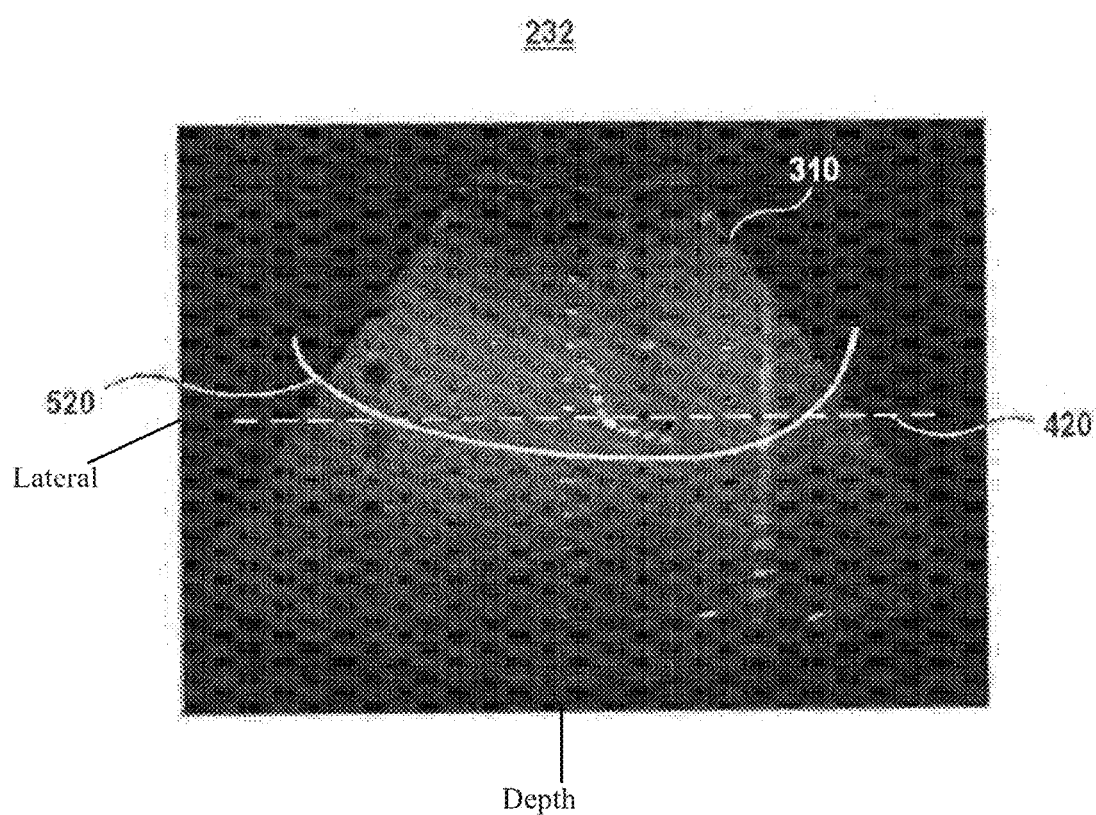
Figure 7:
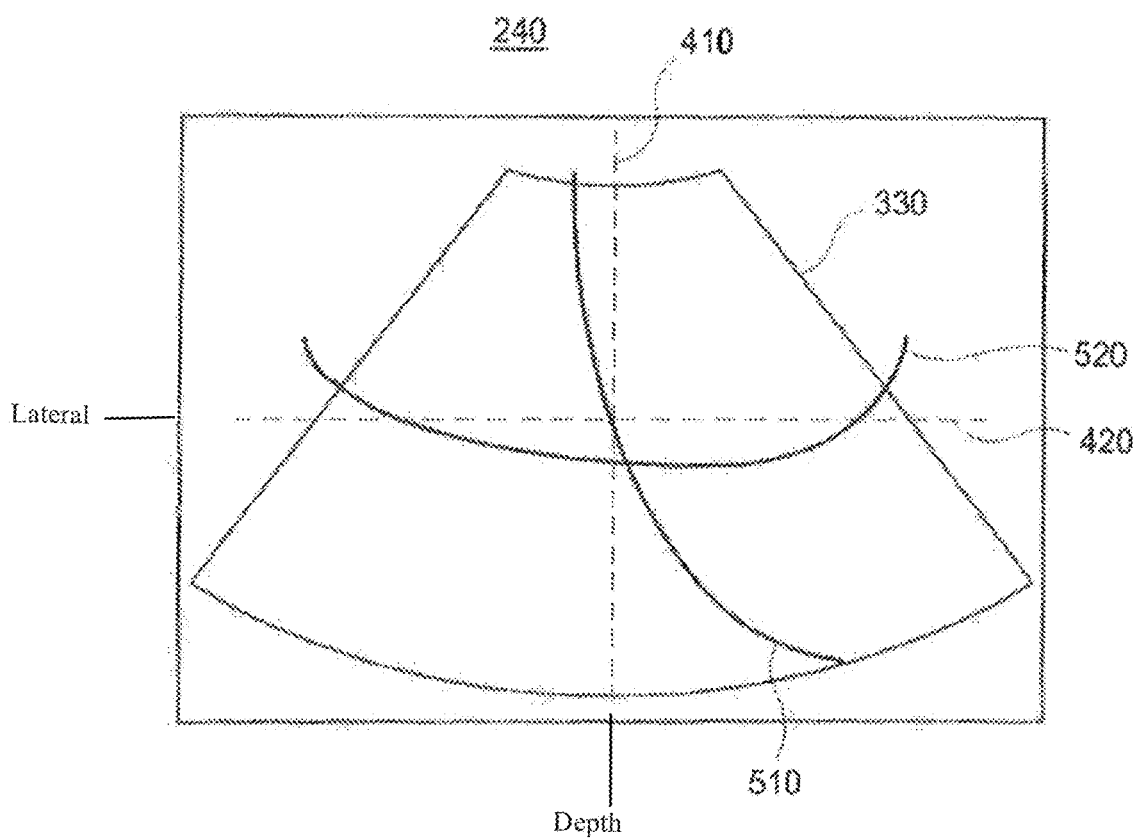

As illustrated in FIG. 2, an ultrasound system 100 comprises: a probe 110; a beam former 120; a signal processing unit 130; a processor 140; a display unit 150; and a TGC/LGC setup unit 160. The probe 110 includes a plurality of transducers 112. Each of the transducers 112 may be configured to transmit an ultrasound signal to an object and receive the ultrasound signal reflected from the object. The beam former 120 may be configured to focus the transmitted ultrasound signals from the transducers 112 on the object and collect the reflected ultrasound signals from the object to the transducers 112 together with corresponding time delay.

The signal processing unit 130 may be configured to amplify the signals collected by the beam former 120 and control gains of the amplified echo signals. Specifically, the signal processing unit 130 may be configured to perform TGC (Time Gain Compensation) and LGC (Lateral Gain Compensation) upon the echo signals based on predetermined TGC and LGC values at a coarse compensation mode (e.g., in an initial operation stage). The signal processing unit 130 may be further configured to perform TGC and LGC upon the echo signals based on TGC and LGC values calculated in a TGC/LGC setup unit 160 using a curve inputted by a user at a fine compensation mode (e.g., during operations).

The processor 140 may be configured to receive the echo signals from the signal processing unit 130 and produce an ultrasound image signal based on the echo signals. The display unit 150 may be adapted to receive the ultrasound image signal from the processor and display an ultrasound image based on the signal.

The TGC/LGC setup unit 160 may include a touch panel 161 and a TGC/LGC setup processor 162.

The touch panel 161 may be configured to display a setup screen and detect TGC/LGC curves inputted by the user on the touch panel 161 to produce a detecting signal. The touch panel 161 detects the user's input according to either the pressure sensing method or the electromagnetic induction method. The touch panel 161 may be a touch panel included in a control panel (not shown) of the ultrasound system 100. Alternatively, it may be separate and apart from the ultrasound system 100.

In one embodiment of the present disclosure, the touch panel 161 may be configured to display a setup screen 210 (shown in FIG. 3) including an ultrasound image 310 and first and second reference lines 410, 420. The ultrasound image 310 is based on the echo signal, the TGC and LGC of which are controlled based on the predetermined TGC and LGC values. The first and second reference lines 410, 420 may be used to detect a TGC curve 510 and a LGC curve 520 inputted by the user (i.e., to determine whether a curve inputted by the user is a TGC curve 510 or a LGC curve 520). After inputting a curve, the user can modify a portion of the curve.

In another embodiment of the present disclosure, the touch panel 161 may be configured to display a setup screen 220 (shown in FIG. 4) including first and second ultrasound images 311, 312 and first and second reference lines 410, 420. The first and second ultrasound images 311, 312 are based on the echo signal, the TGC and LGC of which are controlled based on the predetermined TGC and LGC values. The first and second reference lines 410, 420 may be used to detect whether a curve inputted by the user is a TGC curve 510 or a LGC curve 520. The first ultrasound image 311 may be identical to the second initial ultrasound image 312.

In yet another embodiment of the present disclosure, the touch panel 161 may be configured to display a first setup screen 231 (shown in FIG. 5) including an ultrasound image 310 and a first reference line 410. The ultrasound image 310 is based on the echo signal, the TGC and LGC of which are controlled based on the predetermined TGC and LGC values. The first reference line 410 may be used to detect a TGC curve 510 inputted by the user. The touch panel may then display a second setup screen 232 (shown in FIG. 6) including the ultrasound image 310 and a second reference line 420. The second reference lines 420 may be used to detect a LGC curve 520 inputted by the user. Alternatively, the touch panel 161 may be configured to display the second setup screen 232 before the first setup screen 231.

In still yet another embodiment of the present disclosure, the touch panel 161 may be configured to display a setup screen 240 (shown in FIG. 7) including a virtual ultrasound image 330 and first and second reference lines 410, 420.

The TGC/LGC setup processor 162 may be configured to detect TGC and LGC curves 510, 520 inputted by the user on the touch panel 161. The TGC/LGC setup processor 162 may then calculate new TGC and LGC values in consideration of the detected TGC and LGC curves and transmit the values to the signal processing unit 130.

The TCG/LGC curves 510, 520 are displayed on the touch panel 161 at the time the user inputs the TGC/LGC curves 510, 520. In another embodiment, the TGC/LGC setup processor 162 identifies the user's inputted curves 510, 520 while not displaying the inputted curves 510, 520 on the touch panel. The display unit 150 displays a resultant ultrasound image, which is compensated by the new TGC and LGC values. The user experiences the compensated ultrasound image based on the user's inputted curves 510, 520 without seeing the user's inputted curves 510, 520.

Figure 8:
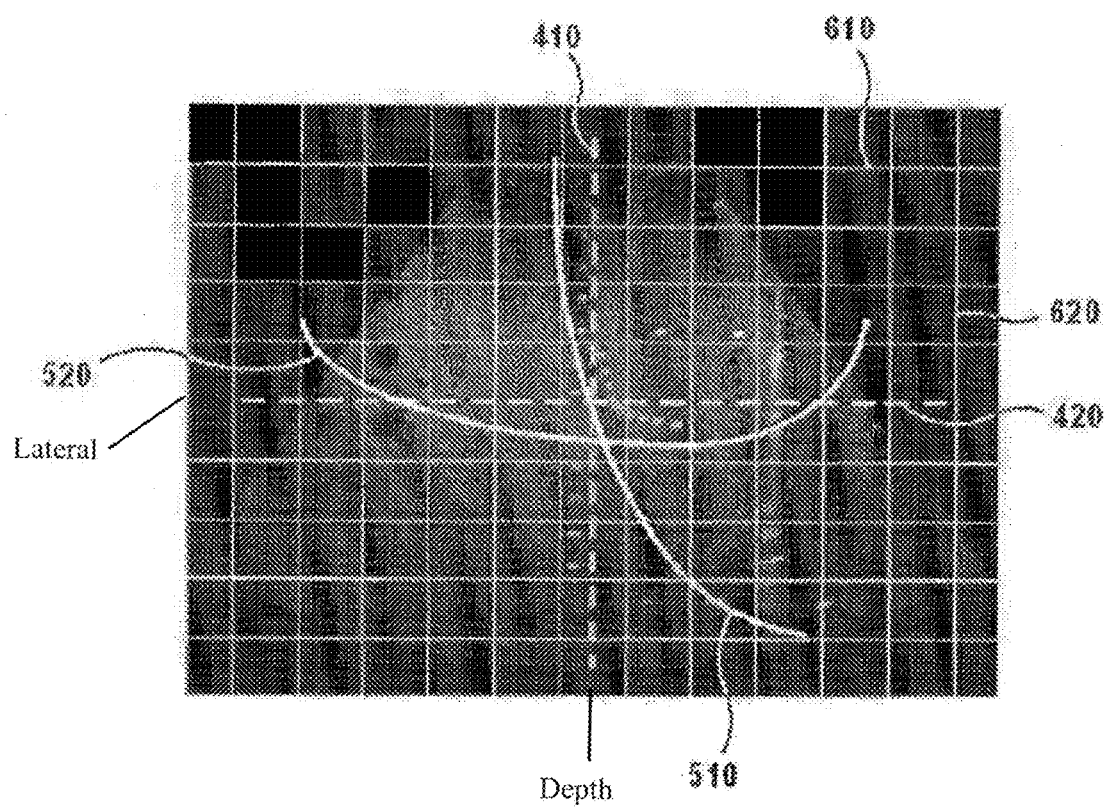
FIG. 8 illustrates an exemplary distinction between TGC and LGC curves according to one embodiment of the present disclosure.

In one embodiment of the present disclosure, as illustrated in FIG. 8, the TGC/LGC setup processor 162 may be configured to establish a first group of lines 610 and a second group of lines 620. The first group of lines 610 is perpendicular to a first reference line 410 and the lines in said group are equally spaced apart from each other. The second group of lines 620 is perpendicular to a second reference line 420 and the lines in this group are equally spaced apart from each other. If it is determined that a curve inputted by the user (such as the curve 510) intersects the first group of lines more often than the second group of lines, then the TGC/LGC setup processor 162 recognizes that the curve is a TGC curve. Alternatively, if it is determined that a curve inputted by the user (such as the curve 520) intersects the second group of lines more often than the first group of lines, then the TGC/LGC setup processor 162 recognizes that the curve is a LGC curve. The TGC/LGC setup processor 162 then calculates the new TGC value corresponding to the TGC curve 510 based on the first reference line 410. It also calculates the LUG value corresponding to the LUC curve 520 based on the second reference line 420. The TGC value and the LGC value are transmitted to the signal processing unit 130.

FIG. 9 illustrates an embodiment of an ultrasound system 200 which employs a probe 110 connected to a portable computer 170. The portable computer 170 may take many forms, including but not limited to a personal computer, workstation, server, network computer, mobile phones and other mobile devices such as smartphones, a pager, a tablet computing device, or other form of computing device equipped with a processor and able to execute ultrasound diagnosis functions.

The portable computer 170 includes a beam former 120; a signal processing unit 130; a processor 140; a display unit 150; and a TGC/LGC setup unit 160 as illustrated in FIG. 2. The beam former 120, the signal processing unit 130, the processor 140, and the display unit 150 and the TGC/LGC setup unit 160 perform the same functions as those in the embodiments of FIGS. 2-8. The touch panel 161 is coupled to the display unit 150 and senses a touch on the display unit 150 inputted by the user. In a smartphone and a tablet PC, a touch screen is implemented with the touch panel 161 and the display unit 150, in combination. The touch panel 161 and the display unit 150, thus, enables the user to interact directly with what is displayed on the display unit 150. In this embodiment, the user inputs the compensation curve and manipulates the ultrasound image via an interface provided by the touch panel 161 and the display unit 162. The beam former 120, and TGC/LGC setup unit 160 may be configured by implementation of a software executed on the signal processing unit 130 or the processor 140.

The portable computer 170 may be connected to the probe 110 via a cable or via a wireless communication link such as a Wi-Fi network, a Bluetooth network, and Near Field Communications. The portable computer 170 may have a wireless communication capability to thereby communicate with another devices or servers over a network 110 such as the Internet, an intranet, LAN (Local Area Network), WAN (Wide Area Network), wireless network or some other type of network over which the portable computer 170 and other related devices can communicate.

Optionally, the portable computer 170 may include multiple CPUs for executing software loaded in memory and other programs for controlling system hardware. The code loaded in the memory may run a program including instructions to perform functions required for the above described TGC or LGC.

Input control for the portable computer 170 may interface with a keyboard, mouse, microphone, camera, such as a web camera, or other input devices such as a 3D mouse, space mouse, multipoint touchpad, accelerometer-based device, gyroscope-based device, etc.

The present invention allows the user to accurately control the TGC and LGC by using the TGC and LGC curves inputted into the touch panel, thereby improving operational accuracy and time. Further, the present invention reduces the size of the control panel to thereby improve the spatial efficiency.

Although the present invention has been described with reference to a number of preferred embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The invention claimed is:

1. An ultrasound diagnosis system, comprising:
 a probe configured to transmit an ultrasound signal to an object and to receive an echo signal reflected from the object; and
 a portable computer configured to generate an ultrasound image of the object, wherein the portable computer includes:
  a touch panel; and
  a processor configured to:
   display, via the touch panel, multiple parallel lines each of which corresponds to two or more positions of the ultrasound image, wherein the multiple parallel lines are visually present on the touch panel;
   generate a curve generated based on a single touch input received via the touch panel in a region of the touch panel in which the multiple parallel lines are displayed, the curve generated based on the single touch input intersecting successively with the displayed multiple parallel lines; and
   adjust compensation setting values of the two or more positions of the ultrasound image, based on the successive intersection of the curve with the displayed multiple parallel lines corresponding to the two or more positions of the ultrasound image,
  wherein the single touch input successively intersects with a plurality of the displayed multiple parallel lines corresponding to the two or more positions, and
  wherein the compensation setting values comprises at least one of a time gain compensation (TGC) value or a lateral gain compensation (LGC) value.

2. The ultrasound diagnosis system of claim 1, wherein the curve generated based on single touch input is not displayed on the touch panel, and the touch panel displays the ultrasound image after the compensation.

3. The ultrasound diagnosis system of claim 1, wherein the curve generated based on the single touch input is displayed on the touch panel.

4. The ultrasound diagnosis system of claim 1, wherein the received single touch input sets a TGC line for setting TGC values or LGC line for setting LGC values.

5. The ultrasound diagnosis system of claim 4, wherein the compensation is a TGC or a LGC depending upon whether the received single touch input related to TGC compensation or LGC compensation.

6. The ultrasound diagnosis system of claim 5, wherein the processor is further configured to perform an initial TGC or LGC based on a predetermined TGC or LGC value before the compensation.

7. The ultrasound diagnosis system of claim 1, wherein the processor is further configured to control the touch panel to display a first reference line and a second reference line, which are perpendicular to each other, used to determine whether the single touch input is a TGC input or a LGC input based on the intersection of the single touch input with the first reference line or the second reference line.

8. The ultrasound diagnosis system of claim 7, wherein the processor is further configured to control the touch panel to further display a first group of lines perpendicular to the first reference line, each of which is spaced apart from adjacent lines at a
 first uniform distance, and a second group of lines perpendicular to the second reference line, each of which is spaced apart from adjacent lines at a second uniform distance.

9. The ultrasound diagnosis system of claim 8, wherein the processor is further configured to determine that the received single touch input is the TGC input when the curve intersects the first group of lines more than the second
 group of lines, and to determine that the received single touch input is the LGC input when the curve intersect the second group of lines more than the first group of lines.

10. The ultrasound diagnosis system of claim 9, wherein the processor is further configured to calculate a new TGC value based on the intersection of the curve with the first reference line if the received single touch input is the TGC input, and to calculate a new LGC value based on the intersection of the curve with the second reference line, if the received single touch input is the LGC input.

11. The ultrasound diagnosis system of claim 10, wherein the processor is further configured to perform compensation based on the new TGC value or the new LGC value.

12. The ultrasound diagnosis system of claim 1, wherein the portable computer is a tablet computer having a touch-type input interface.

13. The ultrasound diagnosis system of claim 1, wherein the portable computer has wireless communication capability.

14. A portable computer, which generates an ultrasound image of an object, the portable computer comprising:
a touch panel; and
a processor configured to:
display, via the touch panel, multiple parallel lines each of which corresponds to two or more positions of the ultrasound image, wherein the multiple parallel lines are visually present on the touch panel;
generate a curve generated based on a single touch input received via the touch panel in a region of the touch panel in which the multiple parallel lines are displayed, the curve generated based on the single touch input intersecting successively with the displayed multiple parallel lines; and
adjust compensation setting values of the two or more positions of the ultrasound image, based on the successive intersection of the curve with the displayed multiple parallel lines corresponding to the two or more positions of the ultrasound image,
wherein the single touch input successively intersects with a plurality of the displayed multiple parallel lines corresponding to the two or more positions, and
wherein the compensation setting values comprises at least one of a time gain compensation (TGC) value or a lateral gain compensation (LGC) value.

15. The portable computer of claim 14, wherein the curve generated based on the single touch input is not displayed on the touch panel, and the touch panel displays the ultrasound image after the compensation.

16. The portable computer of claim 14, wherein the curve generated based on the single touch input is displayed on the touch panel.

17. The portable computer of claim 14, wherein when the single touch input is a TGC input for setting TGC values, the multiple parallel lines are multiple horizontal lines corresponding to two or more depths of the ultrasound image, and
when the single touch input is a LGC input for setting LGC values, the multiple parallel lines are multiple vertical lines corresponding to two or more lateral positions of the ultrasound image.

18. The portable computer of claim 14, wherein the compensation is a TGC or a LGC depending upon whether the received single touch input is related to TGC compensation or LGC compensation.

19. The portable computer of claim 18, wherein the processor is further configured to perform an initial TGC or LGC based on a predetermined TGC or LGC value before the compensation.

20. The portable computer of claim 14, wherein the processor is further configured to control the touch panel to display a first reference line and a second reference line, which are perpendicular to each other, used to determine whether the touch input is a TGC input or a LGC input based on the intersection of the single touch input with the first reference line or the second reference line.

21. The portable computer of claim 20, wherein the processor is further configured to control the touch panel to further display a first group of lines perpendicular to the first reference line, each of which is spaced apart from adjacent lines at a
first uniform distance, and a second group of lines perpendicular to the second reference line, each of which is spaced apart from adjacent lines at a second uniform distance.

22. The portable computer of claim 21, wherein the processor is further configured to determines that the received single touch input is the TGC input when the curve intersects the first group of lines more than the second group of lines, and to determines that the received single touch input is a LGC line when the curve intersect the second group of lines more than the first group of lines.

23. The portable computer of claim 22, wherein the processor is further configured to calculate a new TGC value based on the intersection of the received single touch input with the first reference line if the received single touch input is the TGC input, and to calculates a new LGC value based on the intersection of the received single touch input with the second reference line, if the received single touch input is the LGC input.

24. The portable computer of claim 23, wherein the processor is further configured to perform compensation based on the new TGC value or the new LGC value.

25. The portable computer of claim 14, wherein the portable computer is a tablet computer having a touch-type input interface.

26. The portable computer of claim 14, wherein the portable computer has wireless communication capability.

27. The ultrasound diagnosis system of claim 1, wherein the single touch input is received on a first area of the touch panel and the curve generated based on the single touch input is displayed on a second area of the touch panel, the second area being different from the first area.

28. The ultrasound diagnosis system of claim 1,
wherein the touch panel is further configured to display the ultrasound image in a second area of the touch panel, and
wherein the single touch input is received in a first area of the touch panel, the second area being different from the first area.

29. The portable computer of claim 14, wherein the single touch input is received on a first area of the touch panel and the curve generated based on the single touch input is displayed on a second area of the touch panel, the second area being different from the first area.

30. The portable computer of claim 14,
wherein the touch panel is further configured to display the ultrasound image in a second area of the touch panel, and
wherein the single touch input is received in a first area of the touch panel, the second area being different from the first area.

31. An ultrasound system comprising:
a probe configured to transmit an ultrasound signal to an object and to receive an echo signal reflected from the object; and
a portable computer configured to generate an ultrasound image of the object, wherein the portable computer includes:
a touch panel; and
a processor configured to:
display, via the touch panel, multiple horizontal lines each of which corresponds to two or more depths of the ultrasound image, wherein the multiple horizontal lines are visually present on the touch panel;

generate a curve generated based on a single touch input received via the touch panel in a region of the touch panel in which the multiple horizontal lines are displayed, the curve generated based on the single touch input intersecting successively with the displayed multiple horizontal lines; and adjust TGC values of the two or more depths of the ultrasound image, based on the successive intersection of the curve with the displayed multiple horizontal lines corresponding to the two or more depths of the ultrasound image, wherein the single touch input successively intersects with a plurality of the displayed multiple horizontal lines corresponding to the two or more depths.

32. A portable computer which generates an ultrasound image of an object, the portable computer comprising:

a touch panel; and a processor configured to:

display, via the touch panel, multiple horizontal lines each of which corresponds to two or more depths of the ultrasound image, wherein the multiple horizontal lines are visually present on the touch panel;

generate a curve generated based on a single touch input received via the touch panel in a region of the touch panel in which the multiple horizontal lines are displayed, the curve generated based on the single touch input intersecting successively with the displayed multiple horizontal lines; and adjust the TGC values of the two or more depths of the ultrasound image, based on the successive intersection of the curve with the displayed multiple horizontal lines corresponding to the two or more depths of the ultrasound image, wherein the single touch input successively intersects with a plurality of the displayed multiple horizontal lines corresponding to the two or more depths.

33. An ultrasound diagnosis system comprising:

a probe configured to transmit an ultrasound signal to an object and to receive an echo signal reflected from the object; and a portable computer configured to generate an ultrasound image of the object, wherein the portable computer includes:

a touch panel; and a processor configured to:

display, via the touch panel, multiple vertical lines each of which corresponds to two or more lateral positions of the ultrasound image, wherein the multiple vertical lines are visually present on the touch panel;

generate a curve generated based on a single touch input received via the touch panel in a region of the touch panel in which the multiple vertical lines are displayed, the curve generated based on the single touch input intersecting successively with the displayed multiple vertical lines; and adjust the LGC values of the two or more lateral positions of the ultrasound image, based on the successive intersection of the curve with the displayed multiple vertical lines corresponding to the two or more lateral positions of the ultrasound image, wherein the single touch input successively intersects with a plurality of the displayed multiple vertical lines corresponding to the two or more lateral positions.

34. A portable computer which generates an ultrasound image of an object, the portable computer comprising:

a touch panel; and a processor configured to:

display, via the touch panel, multiple vertical lines each of which corresponds to two or more lateral positions of the ultrasound image, wherein the multiple vertical lines are visually present on the touch panel;

generate a curve generated based on a single touch input received via the touch panel in a region of the touch panel in which the multiple vertical lines are displayed, the curve generated based on the single touch input intersecting successively with the displayed multiple vertical lines; and adjust the LGC values of the two or more lateral positions of the ultrasound image, based on the successive intersection of the curve with the displayed multiple vertical lines corresponding to the two or more lateral positions of the ultrasound image, wherein the single touch input successively intersects with a plurality of the displayed multiple vertical lines corresponding to the two or more lateral positions.

35. An ultrasound diagnosis system comprising:

a probe configured to transmit an ultrasound signal to an object and to receive an echo signal reflected from the object; and a portable computer configured to generate an ultrasound image of the object, wherein the portable computer includes:

a touch panel;

a processor configured to:

display, via the touch panel, multiple parallel lines each of which corresponds to two or more positions of the ultrasound image, wherein the multiple parallel lines are visually present on the touch panel;

generate a curve generated based on a single touch input received via the touch panel in a region of the touch panel in which the multiple parallel lines are displayed, the curve generated based on the single touch input intersecting successively with the displayed multiple parallel lines; and adjust compensation setting values of the two or more positions of the ultrasound image, based on the coordinates of the curve generated base on the single touch input with respect to the displayed multiple parallel lines corresponding to the two or more positions of the ultrasound image, wherein the single touch input successively intersects with a plurality of the displayed multiple parallel lines corresponding to the two or more positions, and wherein the compensation setting values comprises at least one of a time gain compensation (TGC) value or a lateral gain compensation (LGC) value.

36. A portable computer which generates an ultrasound image of an object, the portable computer comprising:

a touch panel; and a processor configured to:

display, via the touch panel, multiple parallel lines each of which corresponds to two or more positions of the ultrasound image, wherein the multiple parallel lines are visually present on the touch panel;

generate a curve generated based on a single touch input received via the touch panel in a region of the touch panel in which the multiple parallel lines are displayed, the curve generated based on the single touch input intersecting successively with multiple parallel lines; and adjust compensation setting values of the two or more positions of the ultrasound image, based on coordinates of the curve generated based on the single touch input with respect to the displayed multiple parallel lines corresponding to the two or more positions of the ultrasound image, wherein the single touch input successively intersects with a plurality of the displayed multiple parallel lines corresponding to the two or more positions, and wherein the compensation setting values comprises at least one of a time gain compensation (TGC) value or a lateral gain compensation (LGC) value.

\* \* \* \* \*